(12) United States Patent
Li et al.

(10) Patent No.: US 10,779,767 B2
(45) Date of Patent: Sep. 22, 2020

(54) ANTENNA FOR AN IMPLANTABLE CARDIAC MONITORING DEVICE

(71) Applicant: PACESETTER, INC., Sylmar, CA (US)

(72) Inventors: Perry Li, Temple City, CA (US); Patrick Kirk, Lone Jack, MO (US); Reza Imani, Moorpark, CA (US); Mitch Goodman, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 360 days.

(21) Appl. No.: 15/233,757

(22) Filed: Aug. 10, 2016

(65) Prior Publication Data

US 2018/0042552 A1 Feb. 15, 2018

(51) Int. Cl.
*A61B 5/042* (2006.01)
*A61B 5/07* (2006.01)
*A61B 5/00* (2006.01)

(52) U.S. Cl.
CPC .............. *A61B 5/686* (2013.01); *A61B 5/042* (2013.01); *A61B 5/076* (2013.01); *A61B 5/6861* (2013.01); *A61B 2562/125* (2013.01)

(58) Field of Classification Search
CPC ......... A61B 5/686; A61B 5/042; A61B 5/076; A61B 5/6861; A61B 2562/125; A61B 5/07; A61B 5/073; A61B 5/0421; A61B 5/04
USPC ....... 600/302, 325, 327, 332, 339, 341, 350, 600/352, 361, 481, 483, 486, 488, 600/508–526, 561
See application file for complete search history.

(56) References Cited

U.S. PATENT DOCUMENTS

| | | | | |
|---|---|---|---|---|
| 5,897,578 A | * | 4/1999 | Wiklund | A61N 1/3752 607/36 |
| 7,317,946 B2 | * | 1/2008 | Twetan | A61N 1/37229 128/903 |
| 7,554,493 B1 | * | 6/2009 | Rahman | H01Q 1/273 343/702 |
| 8,195,305 B2 | * | 6/2012 | Nghiem | A61B 5/0031 607/60 |
| 8,219,204 B2 | * | 7/2012 | Mateychuk | A61N 1/3752 607/60 |
| 8,620,449 B2 | * | 12/2013 | Zhao | A61N 1/37229 343/895 |
| 8,761,896 B2 | * | 6/2014 | Vajha | A61N 1/37229 607/60 |
| 8,849,420 B2 | * | 9/2014 | Kane | A61N 1/05 607/116 |

(Continued)

*Primary Examiner* — Navin Natnithithadha
(74) *Attorney, Agent, or Firm* — The Small Patent Law Group LLC; Dean D. Small (57) ABSTRACT

An implantable cardiac monitoring device and method of manufacture are provided. The device comprises a device housing having electronic components therein. A feedthrough assembly is joined to the device housing. The device comprises an antenna. A header body is mounted to the device housing and encloses the antenna and feedthrough assembly. The antenna includes a pin mounting section and a plate shaped radiating section. The pin mounting and radiating sections are interconnected by a ribbon section having a predetermined length to at least partially tune the antenna to a communication frequency. The radiating section is positioned proximate to, and shaped to extend along, an outer surface of the header body.

18 Claims, 9 Drawing Sheets

(56) References Cited

U.S. PATENT DOCUMENTS

| | | | | |
|---|---|---|---|---|
| 9,259,585 B2* | 2/2016 | Vajha | .................. | A61N 1/37229 |
| 9,265,957 B2* | 2/2016 | Chen | .................. | A61N 1/37223 |
| 9,345,893 B2* | 5/2016 | Kane | ..................... | A61N 1/375 |
| 9,579,509 B2* | 2/2017 | Vajha | .................. | A61N 1/37229 |
| 9,687,661 B2* | 6/2017 | Bortolin | ............... | A61N 1/3752 |
| 9,795,796 B2* | 10/2017 | Bortolin | ............... | A61N 1/3752 |
| 10,004,908 B2* | 6/2018 | Vajha | .................. | A61N 1/37229 |
| 10,029,105 B2* | 7/2018 | Ameri | ............... | A61N 1/37229 |
| 10,099,059 B2* | 10/2018 | Vajha | .................. | A61N 1/37229 |
| 2004/0082977 A1* | 4/2004 | Engmark | ............... | A61N 1/375 |
| | | | | 607/36 |
| 2005/0203583 A1* | 9/2005 | Twetan | .............. | A61N 1/37229 |
| | | | | 607/36 |
| 2005/0203584 A1* | 9/2005 | Twetan | ............... | A61B 5/0031 |
| | | | | 607/36 |
| 2007/0190866 A1* | 8/2007 | Zart | ..................... | A61N 1/3752 |
| | | | | 439/736 |
| 2010/0082080 A1* | 4/2010 | Mateychuk | ........ | A61N 1/37229 |
| | | | | 607/60 |
| 2012/0130206 A1* | 5/2012 | Vajha | ................. | A61N 1/37229 |
| | | | | 600/302 |
| 2012/0130450 A1* | 5/2012 | Vajha | ................. | A61N 1/37229 |
| | | | | 607/60 |
| 2012/0130451 A1* | 5/2012 | Vajha | ................. | A61N 1/37229 |
| | | | | 607/60 |
| 2014/0243930 A1* | 8/2014 | Vajha | ................. | A61N 1/37229 |
| | | | | 607/60 |
| 2014/0364714 A1* | 12/2014 | Ameri | ............... | A61N 1/37229 |
| | | | | 600/373 |
| 2015/0357704 A1* | 12/2015 | Vajha | ................. | A61N 1/37229 |
| | | | | 343/718 |
| 2016/0067504 A1* | 3/2016 | Vajha | ................. | A61N 1/37229 |
| | | | | 607/60 |
| 2017/0056674 A1* | 3/2017 | Bortolin | ............... | A61N 1/3752 |
| 2017/0056675 A1* | 3/2017 | Bortolin | ............... | A61N 1/3752 |
| 2017/0065207 A1* | 3/2017 | Landherr | ............. | A61B 5/0031 |
| 2017/0325741 A1* | 11/2017 | Lim | ....................... | A61B 5/686 |

\* cited by examiner

ANTENNA FOR AN IMPLANTABLE CARDIAC MONITORING DEVICE

BACKGROUND OF THE INVENTION

Embodiments herein generally relate to antenna designs for implantable cardiac monitoring devices.

An implantable cardiac monitoring (ICM) device is a medical device that is implanted in a patient to, among other things, monitor electrical activity of a heart. An ICM device may record cardiac activity of a patient over time and report such cardiac activity to an external device. The ICM device may optionally perform various levels of sophisticated analysis of the cardiac activity and based thereon perform additional recording operations. The ICM device may also be configured to deliver appropriate electrical and/or drug therapy, and as such is also referred to as an implantable medical device (IMD). Examples of IMDs include pacemakers, cardioverters, cardiac rhythm management devices, defibrillators, and the like. The electrical therapy produced by an IMD may include, for example, pacing pulses, cardioverting pulses, and/or defibrillator pulses. The device is used to both provide treatment for the patient and to inform the patient and medical personnel of the physiologic condition of the patient and the status of the treatment.

In general, an ICM includes a battery, memory and electronic circuitry that are hermetically sealed within a metal housing (generally referred to as the "can"). The metal housing typically is formed of titanium and includes a shell with an interconnect cavity, in which the memory, pulse generator and/or processor module reside. The device housing is configured to receive a header assembly. The header assembly comprises a mechanical structure which houses an antenna and a sensing electrode. A feedthrough assembly is located at the header receptacle area and is sealed to the device housing to form an interface for conductors to enter/exit the interconnect cavity.

However, ICM devices have experienced some limitations. Certain types of ICM devices include one or more sensing electrodes and an antenna that are located within the ICM device. For example, the sensing electrode/electrodes and antenna may be located in the header of the ICM device. Heretofore, the header assembly structure joined to the device limits the length of the antenna and limits the placement of the sensing electrode/electrodes relative to the region of interest.

The ICM devices have experienced certain challenges due to the inherently small sizes and operating environment within body tissue. For example, certain challenges exist when designing antenna that satisfy communication signal quality/range requirements and size limitations. More recently, it has been proposed to utilize standard wireless communications protocols, such as Bluetooth or Bluetooth low energy (BLE) protocols. However, existing antenna that support the Bluetooth and BLE protocols with sufficient signal quality/range, do not meet the size limitations of ICM devices.

Further, a mechanical challenge with ICM devices concerns maintaining the header securely connected to the ICM device housing, even though a surface area of the interface there between is extremely small. Typically, the header contains at least an antenna, one or more electrodes and a feedthrough, which affords little additional space to utilize for retention features or other structures to stabilize the header.

A need remains for an improved ICM device that supports the Bluetooth and/or BLE protocols with sufficient signal quality/range, meets the size limitations of ICM device and affords a stable connection between the header and the housing.

SUMMARY

In accordance with embodiments herein, an implantable cardiac monitoring device is provided comprising a device housing having electronic components therein. A feedthrough assembly is joined to the device housing. The device comprises an antenna. A header body is mounted to the device housing and encloses the antenna and feedthrough assembly. The antenna includes a pin mounting section and a plate shaped radiating section. The pin mounting and radiating sections are interconnected by a ribbon section having a predetermined length to at least partially tune the antenna to a communication frequency. The radiating section is positioned proximate to, and shaped to extend along, an outer surface of the header body.

Optionally, the radiating section may be elongated along a longitudinal axis. The axis may be arc shaped to follow a contour of the outer surface of the header body. The ribbon section may have a narrower width than a width of the radiating section. The pin mounting section may be plate shaped and oriented to align with a pin that projects from the feedthrough assembly. The ribbon section may include a zig-zag pattern with a predetermined length. The antenna may be curved with the pin mounting section and radiating section spaced apart to span a height of the header body from the feedthrough assembly to a top edge of the header body. The header body may be formed of an injection molded flowable material that embeds the antenna therein. The radiating section may include one or more mechanical anchoring tabs that may be bent to extend inward and be securely encased within the header body. The electronic components may include a transceiver circuit to communicate with an external device through the antenna utilizing at least one of a Bluetooth protocol or Medical Implant Communications Standard (MICS) protocol.

In accordance with embodiments herein, a method for providing an implantable cardiac monitoring device is provided. The method comprises assembling a device housing having electronic components and joining a feedthrough assembly to the device housing. The method provides an antenna including a pin mounting section and a plate shaped radiating section. The pin mounting and radiating sections are interconnected by a ribbon section having a predetermined length to at least partially tune the antenna to a communications frequency. The method assembles a header body that embeds the antenna therein and orients the antenna within the header body with the radiating section positioned proximate to, and shaped to extend along, an outer surface of the header body.

Optionally, the method may further comprise sizing the radiating section as a rectangular plate with a width that may be wider than a width of the ribbon section to provide large radiating edges long the plate and to provide a stabilizing force for anchoring and retention of the header on the device housing. The providing operation may include shaping the radiating section as an elongated rectangular-shaped plate that extends along a longitudinal axis, and bending the plate along the longitudinal axis in an arc that is shaped to follow a contour of the outer surface of the header body. Further, the operation may include stamping the antenna with the ribbon section to have a narrower width than a width of the radiating sections.

Optionally, the providing operation may include stamping the pin mounting section to have a plate shape and aligning the plate shape with a pin that projects from the feedthrough assembly. The method may further comprise forming a zig-zag pattern in the ribbon section with a predetermined length to at least partially tune the antenna to a frequency of interest. The antenna may include an overall length extending from a proximal end of the pin mounting section to a distal end of the radiating section. The method may further comprise tuning the antenna by adjusting the overall length based on a communications frequency to carry RF signals. The assembling operation may comprise injection molding or casting a flowable material about the antenna.

In accordance with embodiments herein, an antenna is provided in a header of an implantable medical device. The antenna comprises a pin mounting section, a plate shaped radiating section and a ribbon section interconnecting the pin mounting and radiating sections. The ribbon section has a predetermined length to at least partially tune the antenna to a communications frequency. The radiating section has an elongated plate shape that extends along a longitudinal axis. The plate shape is curved along the longitudinal axis to follow a contour of an outer surface of a header.

Optionally, the ribbon section may have a narrower width than a width of the pin mounting and radiating sections. The ribbon section may be curved in a zig-zag pattern. The radiating section may include one or more mechanical anchoring tabs that may be bent to extend inward and securely encased within the header body.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
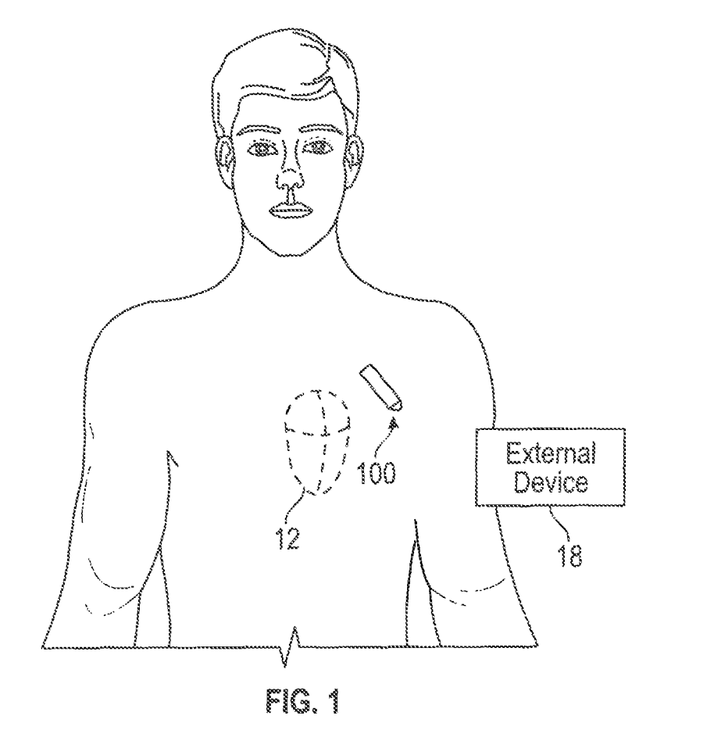
FIG. 1 illustrates an implantable cardiac monitoring (ICM) device intended for subcutaneous implantation at a site near the heart in accordance with embodiments herein.

FIG. 1 illustrates an implantable cardiac monitoring (ICM) device 100 intended for subcutaneous implantation at a site near the heart 12. The ICM device 100 is configured to sense the physiologic signals, such as far field, subcutaneous electrograms. The ICM device 100 is also configured to process the physiologic signals for various characteristics of interest. For example, the ICM device 100 may process electrograms to detect arrhythmias and automatically records the electrograms in memory for subsequent transmission to an external device 18. The physiologic signal processing and detection of characteristics of interest is implemented, at least in part, through algorithms embodied in software and/or firmware that direct the operation of one or more microprocessors.

By way of example, the external device 18 may represent a bedside monitor installed in a patient's home and utilized to communicate with the ICM device 100 while the patient is at home, in bed or asleep. The external device 18 may be a programmer used in the clinic to interrogate the device, retrieve data and program detection criteria and other features. The external device 18 may be a device that can be coupled over a network (e.g. the Internet) to a remote monitoring service, medical network and the like. The external device 18 facilitates access by physicians to patient data as well as permitting the physician to review real-time ECG signals while being collected by the ICM device 100.

Figure 2:
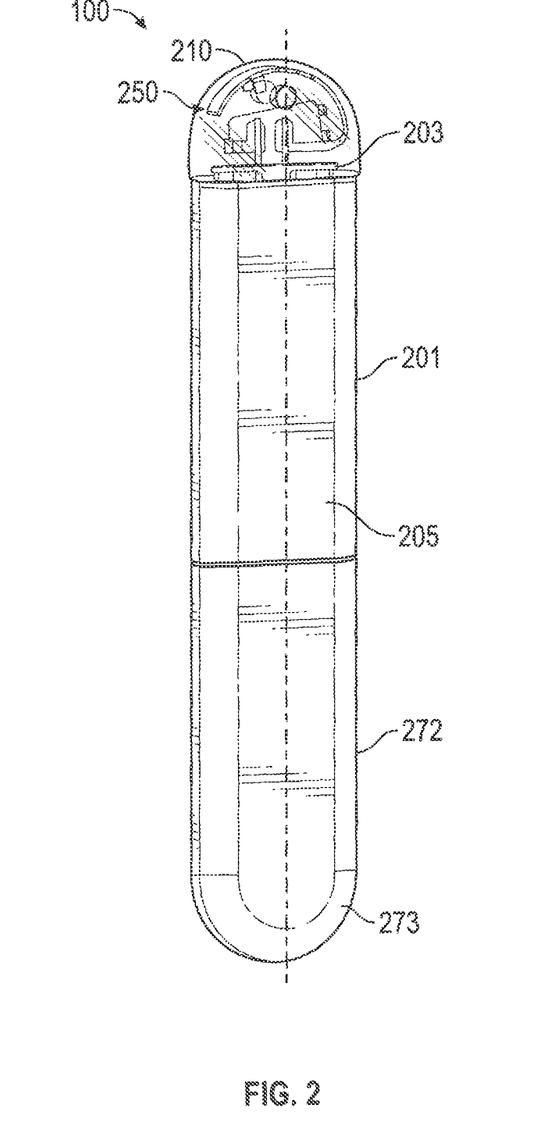
FIG. 2 illustrates a side perspective view of the ICM device formed in accordance with embodiments herein.

FIG. 2 illustrates a side perspective view of the ICM device 100 formed in accordance with embodiments herein. The ICM device 100 includes a housing 201 that is elongated and extends along a longitudinal axis 205. The housing 201 includes a feedthrough assembly 203 secured to one end of the housing 201. A header 210 is securely mounted on the feedthrough assembly 203 and the corresponding end of the housing 201. In the embodiment of FIG. 2, the housing 201 is, with the header 210 joined to one end of the housing 201. Optionally, the housing 201 may be formed with alternative shapes. The header 210 includes an antenna 250 and one or more electrodes 232. The electrode 232 is electrically isolated from the housing 201. All or a portion of the housing 201 may be utilized as a separate electrode. Optionally, the ICM device 100 may include multiple sensing electrodes 232 positioned in the header 210 and/or at select points about the housing 201. The electrodes 232 may be located in various locations on the housing 201 based on the shape of the ICM device 100, the implant location, the intended use of the ICM device 100 and the like. For example, when separate housing portions are provided for the electronic components and the battery, one or more electrodes may be located on the housing portion that holds the battery 272 (e.g., the battery housing).

Figure 3:
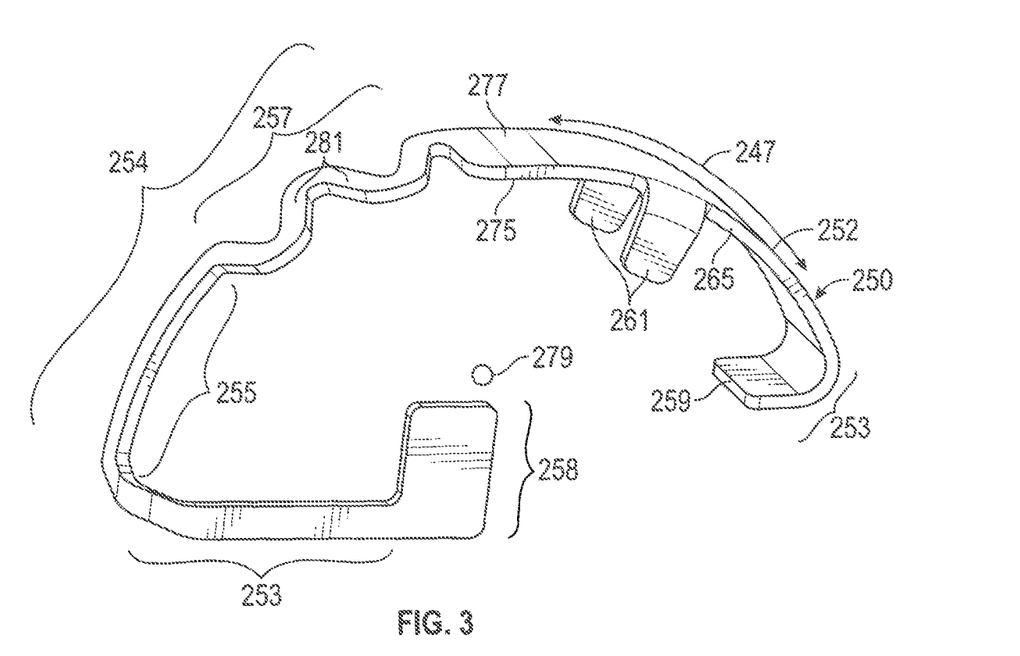
FIG. 3 illustrates an isolated perspective view of an antenna formed in accordance with an embodiment herein.

FIG. 3 illustrates an isolated side perspective view of the antenna 250 formed in accordance with an embodiment herein. The antenna 250 includes a plate shaped radiating section 252 and a pin mounting section 258. The radiating section 252 and pin mounting section 258 are interconnected by the ribbon section 254. The ribbon section 254 includes an initial base stem segment 253 that is generally linear. The base stem segment 253 is joined at one end to the pin mounting section 258 and is joined at an opposite end to a leg segment 255. The leg segment 255 is arcuate along a path that parallels the curvature of a peripheral edge 222 of the header body 212. The leg segment 255 has a distal end that is joined to a winding segment 257. The base stem, leg and winding segments 253, 255, 257 are formed integral with one another and with the pin mounting section 258 radiating section 252, such as through a stamping and forming operation. Optionally, the pin mounting section 258, ribbon section 254 and radiating section 252, as well as the base stem, leg and winding segments 253, 255, 257, may be formed in other manners, such as through molding, machining techniques and the like. During transmission, an RF signal is supplied from the pin 206 (FIG. 4A) at the feedthrough. The RF signal travels along the ribbon section 254, which includes the base stem segment 253, the leg segment 255 and the winding segment 257, all of which have a common cross section.

The ribbon section 254 and radiating section 252 include an interior surface 275 and an exterior surface 277 relative to a center 279 of the U-shaped arc in the antenna 250. The interior and exterior surfaces 275 and 277 are arranged concentric within one another, and curve along an arc, relative to the center 279, such that the interior and exterior surfaces 275 and 277 follow the contour of the edge 222 of the header body 212. The antenna 250 is curved with the pin mounting section 258 and radiating section 252 spaced apart to span a height 287 (FIG. 4A) of the header body 212 from the feedthrough assembly 203 to an edge 222 of the header body 212.

The radiating section 252 includes an outer distal tip 259 bent to form a hook shaped segment 263. Tabs 261 are provided along the lateral edges 265 of the radiating section 252. The tabs 261 are bent inward or downward toward a central portion of the antenna 250. The hook shaped segment 263 and tabs 261 facilitate assembly of the antenna 250. The radiating section 252 is bent along an arcuate path 247 that substantially conforms to the shape of the outer distal surface of the header body 212.

Figure 4A:
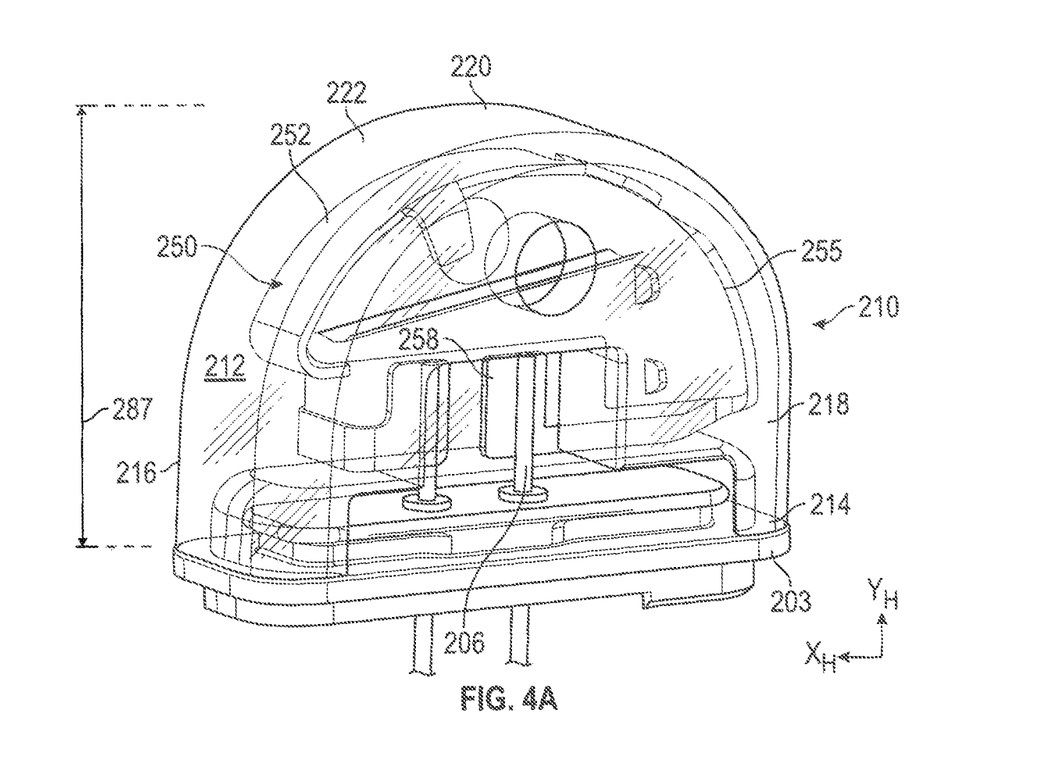
FIG. 4A illustrates a side perspective view of a header to be assembled with the ICM device in accordance with embodiments herein.
Figure 4B:
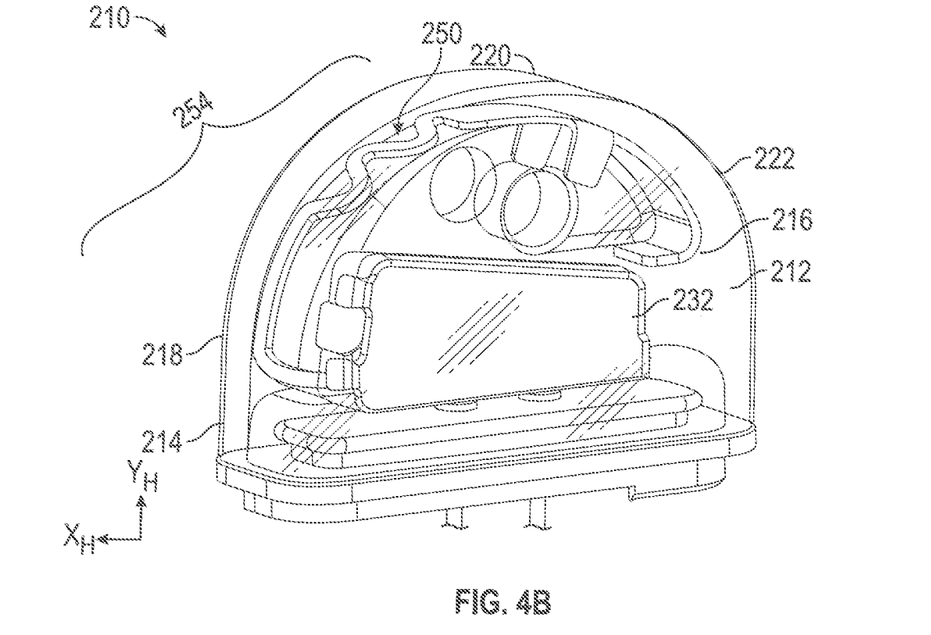
FIG. 4B illustrates a side perspective view of the header from a side opposite to the perspective of FIG. 4A in accordance with embodiments herein.
Figure 4C:
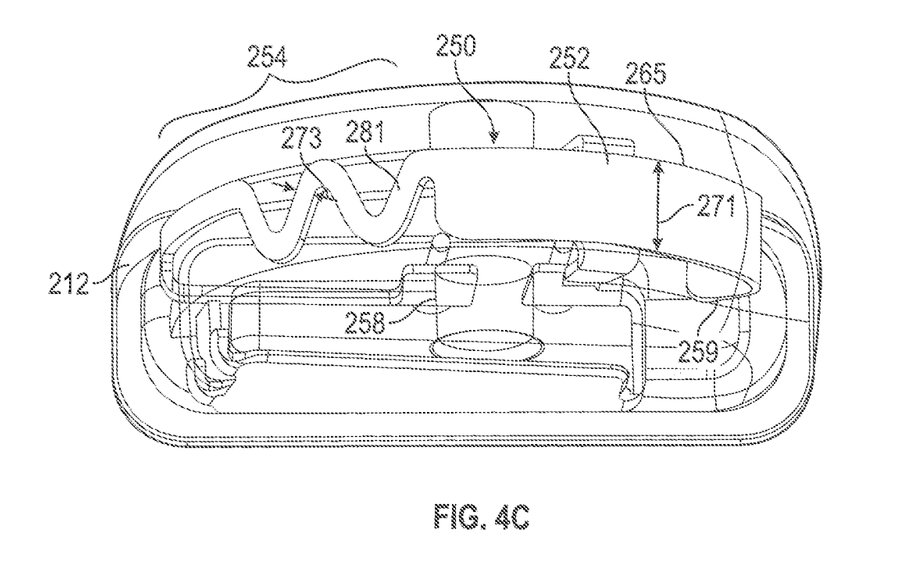
FIG. 4C illustrates a top perspective view of a header to be assembled with the ICM device in accordance with embodiments herein.

FIGS. 4A-4C illustrate perspective views of the header 210 from different angles with the header body 212 shown in a partially transparent manner to facilitate illustration of the internal components. FIGS. 4A and 4B illustrate opposite side perspective views of the header 210 formed in accordance with embodiments herein, while FIG. 4C illustrates a top plan view of the header 210.

The header 210 includes, among other things, the antenna 250 and an electrode 232 (FIG. 4B). FIGS. 4A and 4B illustrate the internal structures of the header 210 from opposite sides, primarily illustrating the antenna 250 from opposite side views. The header body 212 is formed in a semicircular or half-moon shape with generally flat opposed sides 216, 218 (e.g., similar to half of a hockey puck or disk). The header body 212 includes a housing mounting surface 214 that is configured to be mounted on, and secured to, the feedthrough assembly 203 that is joined to the end of the housing 201 (FIG. 2). The header body 212 further includes a half-moon or C-shaped peripheral edge 222 that is formed in a curve. The edge 222 wraps in an arc and includes a distal surface 220 that is remote from the housing mounting surface 214. The edge 222, distal surface 220 and opposed sides 216, 218 merge with one another along smooth beveled regions to form half of a hockey puck or disk shaped structure having a thickness corresponding to the distance between the opposed sides 216, 218. The smooth beveled edges afford a smooth overall contour for the header body 212. The opposite sides 216, 218 are generally planar and oriented to extend parallel to the longitudinal axis and a header plane (as designated by arrows $X_H$ and $Y_H$).

FIG. 4B illustrates the side 216, while the side 218 is not visible. The side 216 perspective makes visible at least one sensing electrode 232 located proximate to the side 216. The sensing electrode 232 is generally planar and oriented to extend along the side 216. However, it is understood that the electrode 232 may be constructed in various shapes, oriented in different manners and positioned in different locations within the header body 212. FIGS. 4A and 4B also illustrate one configuration for the antenna 250, wherein the antenna 250 extends along the edge 222 of the header body 212.

FIG. 4C illustrates a top perspective view of the header 210. A radiating section 252 is formed in a generally rectangular shape with opposed lateral edges. The ribbon section 254 and radiating section 252 include lateral edges 265. The lateral edges 265 of the ribbon section 254 are spaced a constant first distance (width) 273 from one another along the length of the ribbon section 254. The lateral edges 265 of the radiating section 252 are spaced a constant second distance (width) 271 from one another along the length of the radiating section 252, wherein the first and second distances differ from one another. Optionally, the lateral edges 265 of the ribbon section 254 are spaced closer (distance 273) to one another than the distance 271 between the lateral edges 265 of the radiating section 252.

The ribbon section 254 has a cross section that remains relatively uniform at any select point along the base stem, leg and winding segments 253, 255, 257. The uniform cross section enables the ribbon section 254 to maintain relatively constant electrical properties along a length thereof. The cross section of the ribbon section 254 is defined by a height and the width 273. The height of the cross section corresponds to the distance between the interior and exterior surfaces 275, 277 (FIG. 3). The width 273 of the cross section of the ribbon section 254 corresponds to a distance between the lateral edges 265 of the ribbon section 254. The cross section of the ribbon section 254 differs from the cross section of the radiating section 252. For example, the difference in cross sections between the ribbon section 254 and the radiating section 252 may be determined based in part of the transmission properties of interest.

While traveling through the ribbon section 254, very little energy from the RF signal is irradiated from the antenna 250. Once the RF signal reaches the radiating section 252, the RF signal begins to decouple and begins to irradiate from the lateral edges 265. The RF signal also irradiates from the distal end 259. To increase the efficiency of signal propagation, the lateral edges 265 spaced laterally apart from one another by a distance that is greater than the lateral width of the conductor along the ribbon section 254. For example, the lateral width (as measured in the direction of arrow 271) may be two or more times greater than the lateral width 273 of the conductor along the ribbon section 254. As a further example, the lateral width 271 of the radiating section 252 may be three or more times greater than the lateral width 273 of the conductor in the ribbon section 254.

In addition, by widening the lateral width 271, more area is added to provide stabilizing features to couple the antenna 250 to the header body 212. Anchoring and retention features can be introduced into the rectangular section of the antenna 250 to help strengthen the attachment of the header 210 to the housing 201. The radiating section 252 is also lengthened in order to serve as a better frame for the header during the extraction process (e.g., when it becomes desirable to explant the device).

Optionally, the shape of the ribbon section 254 may be varied, such as by providing a varying cross-section along the length thereof. For example, the width and/or height may change along the length of the ribbon section 254, such as by providing a gradual increase in the width and/or height while propagating along the length of the ribbon section 254. Additionally or alternatively, the base stem segment 253 may have a cross section with a different width and/or height, as compared to the width or height of the leg segment 255. Additionally or alternatively, the leg segment 255 may have a cross section with a different width and/or height, as compared to the width or height of the winding segment 257.

The ribbon section 254 includes a predetermined number of curved links 281 in the winding segment 257. The number and shape of the curved links 281 is based on a desired predetermined length to be achieved. The number and shape of the curved links 281 may be varied based on the predetermined length that is desired. The links 281 expand the conductive path that is followed by the RF signals by a first distance, while preventing the overall physical length of the ribbon section 254 from increasing by an equal corresponding distance. For example, the links 281 may add a distance X to the conductive path followed by the RF signals, but only increase the overall physical length of the ribbon section 254 by 10% to 90% of X. For example, if it is assumed that the links 281 have a conductive path of 20 mm (or more), the physical length of the winding segment 257 may be less than 20 mm (e.g., 10% to 90% of 20 mm). It is recognized that 20 mm is merely By way of example, the antenna 250 may represent a monopole antenna that is generally formed as a wire antenna connected at one end to an RF feedthrough pin and is open at the other end. RF signals are conducted from the RF feedthrough pin to the antenna to the open end where the signal is radiated into space. Monopole antennas are considered one basic type of antenna that is flexible to use and relatively easy to implement. At least one technical effect of the embodiments herein, presents modified versions of a monopole antenna with select features to allow smaller sizing than a traditional monopole. The special features also allow the antenna to function as a mechanical frame and anchor for the material forming the header (e.g., epoxy or another similar material). However, it is understood that the principles described herein may be applied to other types of antenna such as dipole antenna as well as other types of antenna.

In accordance with at least one embodiment herein, a type of monopole antenna presented may constitute a strip of sheet metal divided into different sections. The first section (pin mounting section 258) is a square/rectangular plate that allows the antenna to be welded to the RF feedthrough pin extending from the feedthrough assembly. The second section is a long, narrow ribbon section 254 used to help tune the antenna to a desired frequency. The length of the antenna is directly related to the frequency of operation, and thus the second "ribbon" section can be adjusted to be longer or shorter depending on the communications standard being used (e.g., whether using a carrier frequency associated with the Medical Implant Communications Standard (MICS), a Bluetooth protocol, the Bluetooth low energy protocol or otherwise). The third (radiating) section 252 is a larger plate at the open end of the antenna that serves to help radiate the RF signal into open space. The radiating section 252 is formed with a larger plate size to facilitate better radiation efficiency. In accordance with at least some embodiments, another technical effect is the combination of the tunable long narrow ribbon with the better radiating large rectangular plate end to allow the antenna to exhibit performance that is equivalent to other antennas that have a much larger form factor, such as in an implantable cardioverter-defibrillator (ICD).

In accordance with some embodiments, to obtain the select level of performance, the antenna extended as far as practical from the end of the housing (e.g., device can), in order to present a larger overall antenna profile for sending and receiving signals. Thus, the ICM device antenna may exhibit a preferred performance (e.g., optimal performance) when the radiating section is routed along the outer edge of the header body. In addition, another technical effect of certain embodiments is that extending the length of the antenna along the outer edge of the header body also allows the antenna to serve as a frame and reinforcement for the header during explant procedure. To better serve this role, the rectangular portion of the antenna is made longer than necessary to travel farther along the header edge. To also provide reinforcement during explant in accordance with some embodiments, tab features are inserted onto the antenna ribbon for better adhesion and reinforcement of antenna in the header. The different features are easily adjustable to obtain better RF performance or better fit within the header.

As illustrated in FIGS. 4A-4B, the ribbon section 254 and radiating section 252 are positioned proximate to, and shaped to extend along, an outer surface of the header body 212 (corresponding to the edge 222). For example, the ribbon section 254 and radiating section 252 may be formed in a U-shape or C-shape that bends about a virtual center 279. Optionally, the ribbon and radiating sections 254, 252 may be formed in alternative shapes.

The ribbon section 254 is sized and dimensioned to have a predetermined length to at least partially tune the antenna 250 to a select frequency, without unduly expanding the physical length of the antenna 250. The ribbon section 254 is configured to provide the antenna 250 with adequate overall conductive path length based on a desired communications frequency. For example, in certain applications, the antenna 250 may be tuned to communicate at a select frequency of 400 MHz or 2.4 GHz. The antenna 250 may be constructed to support communications in accordance with a Bluetooth protocol, a Wi-Fi protocol, or various other wireless protocols. As a further example, the antenna 250 may be formed with an electrical length that corresponds approximately to (or is greater than) a quarter wavelength of the desired frequency. For example, when the antenna 250 operates at the frequency of 2.4 GHz, the antenna 250 may be constructed with an overall length of approximately 1.25 inches. Optionally, the antenna 250 may be constructed to have a length corresponding to or greater than one half of the wavelength of the desired frequency. For example, when utilizing the frequency of 2.4 GHz, the antenna overall length may be approximately 2.5 inches. As a further example, the antenna 250 may have a length that is equal to or greater than the wavelength of the desired frequency. The overall length of the antenna is measured from the distal tip 259 to the point along the pin mounting section 258 that intersects a pin extending through the feedthrough assembly 203 (as is evident in FIG. 4A).

Figure 5:
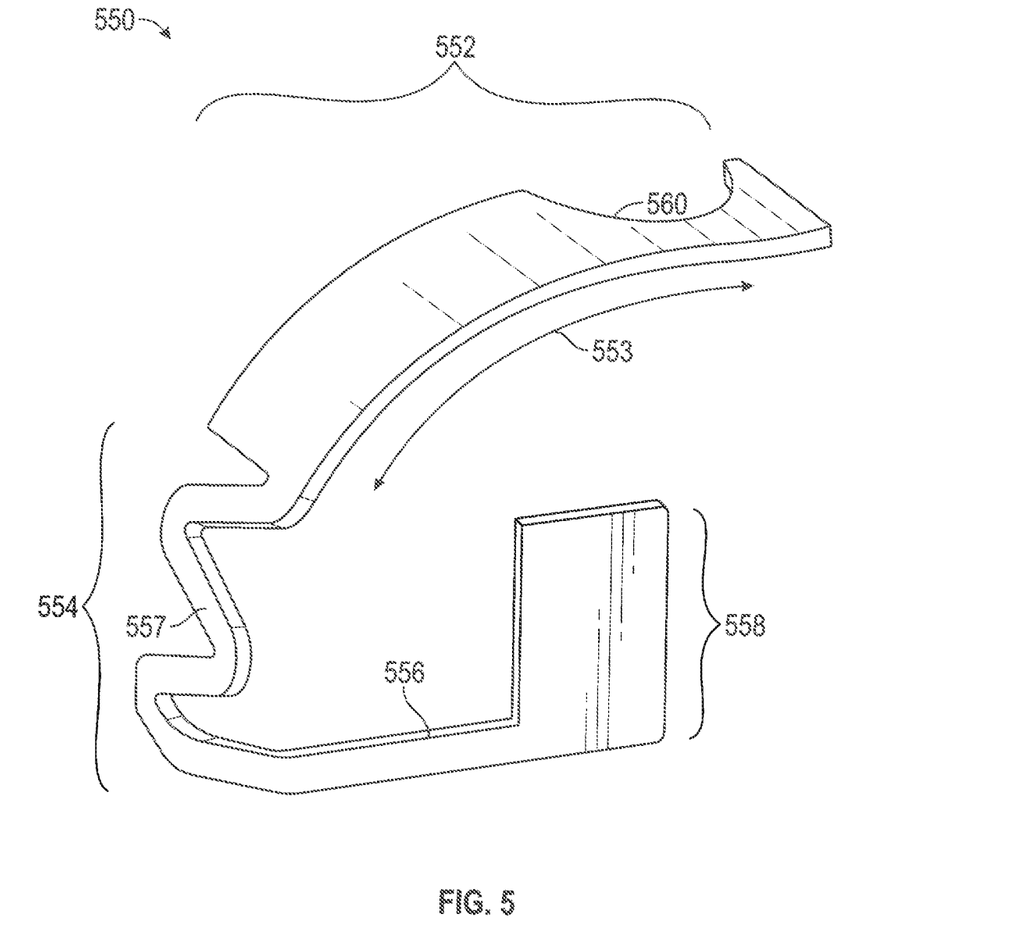
FIG. 5 illustrates an isolated view of an antenna with weld pad, zig-zag pattern in the ribbon section and rectangular plate formed in accordance with an embodiment herein.

FIG. 5 illustrates a side perspective view of an antenna 550 formed in accordance with an alternative embodiment herein. The antenna 550 includes a radiating section 552 and a pin mounting section 558, with a ribbon section 554 interconnected between. The ribbon section 554 includes a base stem segment 556 and a winding segment 557. The winding segment 557 is formed with a zig-zag pattern. Optionally, the winding segment 557 may be formed with a serpentine or S-shape. Optionally, the winding segment 557 may be formed with alternative tortuous paths. The ribbon section 554 does not include a segment similar to the leg segment of FIG. 3. The radiating section 552 is formed in a generally rectangular shape, while bending along an arcuate path 553 that substantially conforms to the shape of the outer distal surface of the header body (e.g., edge 222 of the header body 212). The radiating section 552 includes a semicircular notched out portion 560 that is shaped and positioned to provide select transmission and reception characteristics. Optionally, the radiating section 552 and the notched out portion 560 may be formed with alternative shapes based upon the particular design constraints and wireless protocol.

Figure 6:
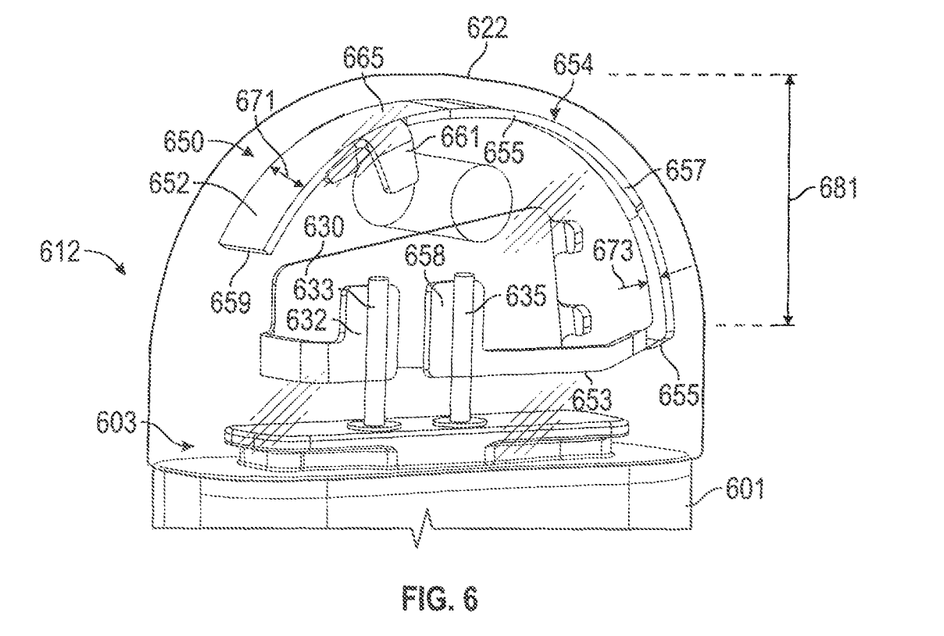
FIG. 6 illustrates a side perspective view of a header to be assembled with the ICM device in accordance with alternative embodiments herein.

FIG. 6 illustrates a header 612 and antenna 650 formed in accordance with an alternative embodiment. The header 612 is joined to a housing 601 at a feedthrough assembly 603. FIG. 6 illustrates the interconnections between feedthrough pins 635, 633, an electrode 630, and the antenna 650 in accordance with an embodiment herein. The radiating and pin mounting sections 652, 658 are interconnected by a ribbon section 654. The ribbon section 654 includes an initial base stem segment 653 that is generally straight or linear. The base stem segment 653 is joined at one end to the pin mounting section 658 and is joined at an opposite end to a leg segment 655. The leg segment 655 is arcuate along a path that parallels the curvature of the edge 622 of the header body 612. The leg segment 655 has a distal end that is joined to the radiating section 652. The base stem and leg segments 653, 657 are formed integral with one another and with the pin mounting and radiating sections 658 and 652, such as through a stamping and forming operation. In the example of FIG. 6, no winding segment is included as the direct physical length of the ribbon section 654 is sufficient to satisfy the conductive path requirements of the antenna 650.

Optionally, the base stem segment 653 may include one or more curved links such as in the winding segment 257. Optionally, curved links may be separated and distributed along the length of the ribbon section with straight or linear segments there between.

The ribbon section 654 and radiating section 652 are along an arc, relative to a center point to follow the contour of the edge 622 of the header body 612. The ribbon section 654 and radiating section 652 includes lateral edges 665. The lateral edges 665 of the ribbon section 654 are spaced a constant first distance (width) 673 from one another along the length of the ribbon section 654. The lateral edges 665 of the radiating section 652 are spaced a constant second distance (width) 671 from one another along the length of the radiating section 652. In the example of FIG. 6, the first and second distances 673 and 671 differ from one another. Optionally, the distances 673 and 671 may be the same. In the example of FIG. 6, the lateral edge 665 visible (in the front) is continuous such that the front lateral edge 665 of the ribbon section 654 aligns with the front lateral edge 665 of the radiating section 652. The lateral edge 665 hidden (in the back) is stepped at the interface between the ribbon section 654 and the radiating section 652.

The radiating section 652 includes an outer distal tip 659. However, the distal end 659 does not include the hooked segment (as in FIGS. 3A-3C). Tabs 661 are provided along the lateral edges 665 of the radiating section 652. The tabs 661 are bent inward or downward toward a central portion of the antenna 650. The radiating section 652 is bent along an arcuate path that substantially conforms to the shape of the outer distal surface of the header body 612.

The pin mounting section 658 is physically and conductively coupled to a feedthrough pin 635. The electrode 630 includes an electrode pin mounting section 632 that is physically and conductively coupled to a feedthrough pin 633. The pins 633 and 635 extend through the feedthrough assembly 603 into the housing 601 where the pins 633 and 635 couple to corresponding sensing and communications circuits. Optionally, the pins 633, 635 may be connected within the housing 601 to a switch that selectively connects to sensing and communications circuits.

Optionally, FIG. 6 illustrates an embodiment for higher desired frequencies, where the zig-zag patterns or winding segments have been removed and replaced with a straight segment. By including or excluding all, some or select numbers of links in the winding segment, various embodiments herein afford an antenna design with a high degree of flexibility with regard to frequency tuning. To achieve a desired antenna length as well as a preferred radiation efficiency, the antenna may be shaped to span the full height (e.g., as noted at 681 in FIG. 6) of the header 612 from the feedthrough 603 to the top of the edge 622.

Figure 7:
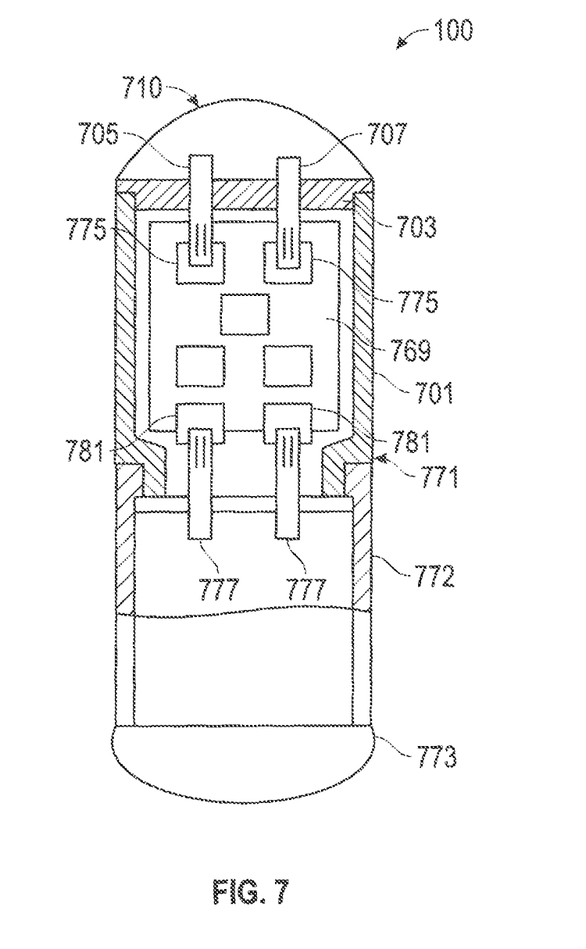
FIG. 7 illustrates a cross-sectional view of an ICM device 100 formed in accordance with an embodiment herein.

FIG. 7 illustrates a simplified block diagram of an ICM device 100 formed in accordance with an embodiment herein. The ICM device 100 includes the header 710 attached to one end of the housing 701, while the opposite end of the housing 701 is connected to a battery 772. An electrode 773 is provided on an exterior surface of the battery 772. Pins 777 connect the battery 772 to pads 781 on the board 769. By way of example, an open end 771 of the housing 701 is tapered to fit within an opening in an end of the battery 772, with an interface there welded to form a seal. The housing 701 encloses memory and electronics on one or more circuit boards 769 that are coupled to conductors 705, 707. The conductors 705, 707 extend through the feedthrough assembly 703 and attach to pads 775 on the board 769. A ground connection is also maintained between the feedthrough assembly 703 and the circuit board 769. It is understood that the example of FIG. 7 represents one exemplary construction, while ICM devices may be constructed with numerous alternative shapes and combinations of components therein.

Figure 8:
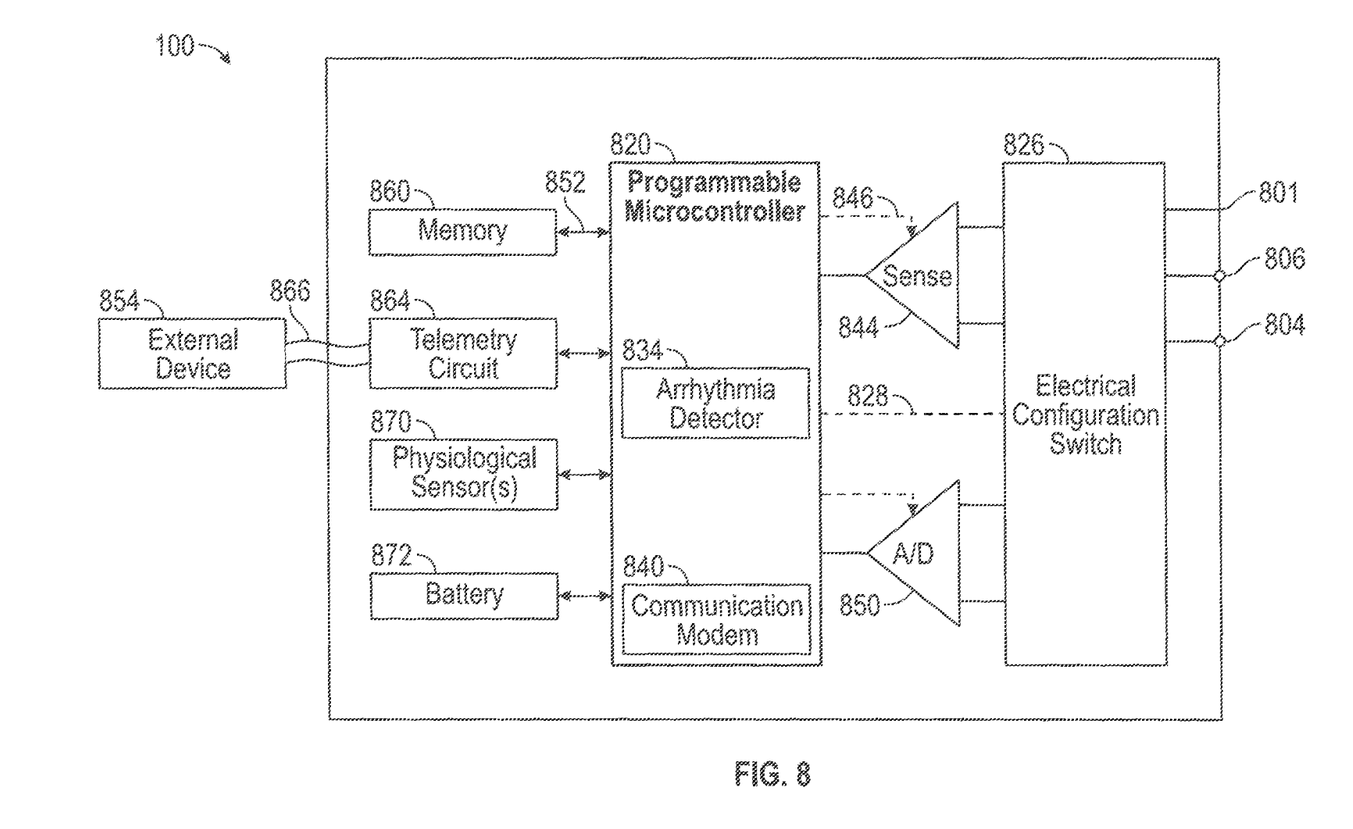
FIG. 8 illustrates a block diagram of an exemplary ICM device that is configured to be implanted into the patient in accordance with embodiments herein.

FIG. 8 illustrates a block diagram of an exemplary ICM device 100 that is configured to be implanted into the patient. Optionally, the ICM device 100 may be provided as an external device that is worn, held or otherwise located proximate to the patient during operation. The ICM device 100 may be implemented to monitor ventricular activity alone, or both ventricular and atrial activity through sensing circuitry. The ICM device 100 has a housing 801 (FIG. 2) to hold the electronic/computing components. The housing 801 (which is often referred to as the "can", "case", "encasing", or "case electrode") may be programmably selected to act as an electrode for certain sensing modes. Housing 801 further includes a connector (not shown) with at least one terminal 806 and preferably a second terminal 804. The terminals 806, 804 may be coupled to sensing electrodes (on the device housing, in the header, or located otherwise) that are provided upon or immediately adjacent the housing 801. Additionally or alternatively, the terminals 806, 804 may be connected to one or more leads having one or more electrodes provided thereon, where the electrodes are located in various locations about the heart. The type and location of each electrode may vary.

The ICM device 100 is configured to be placed subcutaneously utilizing a minimally invasive approach. Subcutaneous electrodes are provided on the housing 801 to simplify the implant procedure and eliminate a need for a transvenous lead system. The sensing electrodes may be located on opposite sides/ends of the device and designed to provide robust episode detection through consistent contact at a sensor-tissue interface. The ICM device 100 may be configured to be activated by the patient or automatically activated, in connection with recording subcutaneous ECG signals.

The ICM device 100 includes a programmable microcontroller 820 that controls various operations of the ICM device 100, including cardiac monitoring. Microcontroller 820 includes a microprocessor (or equivalent control circuitry), RAM and/or ROM memory, logic and timing circuitry, state machine circuitry, and I/O circuitry. The microcontroller 820 also performs the operations in connection with collecting cardiac activity data and analyzing the cardiac activity data to identify episodes of interest. Microcontroller 820 includes an arrhythmia detector 834 that is configured to analyze cardiac activity data to identify potential AF episodes as well as other arrhythmias (e.g. Tachycardias, Bradycardias, Asystole, etc.).

A switch 826 is optionally provided to allow selection of different electrode configurations under the control of the microcontroller 820. The switch 826 is controlled by a control signal 828 from the microcontroller 820. Optionally, the switch 826 may be omitted and the I/O circuits directly connected to the housing electrode and a second electrode.

The ICM device 100 is further equipped with a telemetry circuit 864 and a communication modem (modulator/demodulator) 840 to enable wireless communication. In one implementation, the telemetry circuit 864 and communication modem 840 use high frequency modulation, for example using RF or Blue Tooth telemetry protocols. The telemetry circuit 864 may include one or more transceivers. For example, the telemetry circuit 864 may be coupled to an antenna in the header that transmits communications signals in a high frequency range that will travel through the body tissue in fluids without stimulating the heart or being felt by the patient. The communication modem 840 may be implemented in hardware as part of the microcontroller 820, or as software/firmware instructions programmed into and executed by the microcontroller 820.

The ICM device 100 includes sensing circuitry 844 selectively coupled to one or more electrodes that perform sensing operations, through the switch 826 to detect cardiac activity data indicative of cardiac activity. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. In one embodiment, switch 826 may be used to determine the sensing polarity of the cardiac signal by selectively closing the appropriate switches.

The output of the sensing circuitry 844 is connected to the microcontroller 820 which, in turn, determines when to store the cardiac activity data (digitized by the A/D data acquisition system 850) in the memory 860. The sensing circuit 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

The microcontroller 820 is coupled to a memory 860 by a suitable data/address bus 862. The programmable operating parameters used by the microcontroller 820 are stored in memory 860 and used to customize the operation of the ICM device 100 to suit the needs of a particular patient. Such operating parameters define, for example, detection rate thresholds, sensitivity, automatic features, arrhythmia detection criteria, activity sensing or other physiological sensors, and electrode polarity, etc. The operating parameters of the ICM device 100 may be non-invasively programmed into the memory 860 through a telemetry circuit 864 in telemetric communication via communication link 866 with the external device 854 (which may correspond to external device 18 in FIG. 1). The telemetry circuit 864 allows intracardiac electrograms and status information relating to the operation of the ICM device 100 (as contained in the microcontroller 820 or memory 860) to be sent to the external device 854 through the established communication link 866.

The ICM device 100 can further include one or more physiologic sensor 870. The physiological sensor 870 may further be used to detect changes in the physiological condition of the heart, or diurnal changes in activity (e.g., detecting sleep and wake states). Signals generated by the physiological sensors 870 are passed to the microcontroller 820 for analysis and optional storage in the memory 860 in connection with the cardiac activity data, markers, episode information and the like. Examples of physiologic sensors might include sensors that, for example, detect activity, temperature, sense respiration rate, pH of blood, ventricular gradient, activity, position/posture, minute ventilation (MV), and so forth.

A battery 872 provides operating power to all of the components in the ICM device 100. The battery 872 is capable of operating at low current drains for long periods of time. The battery 872 also desirably has a predictable discharge characteristic so that elective replacement time can be detected. As one example, the device 100 employs lithium/silver vanadium oxide batteries. The battery 872 may afford various periods of longevity (e.g. three years or more of device monitoring). In alternate embodiments, the battery 872 could be rechargeable. See for example, U.S. Pat. No. 7,294,108, Cardiac event microrecorder and method for implanting same, which is hereby incorporated by reference.

Figure 9:
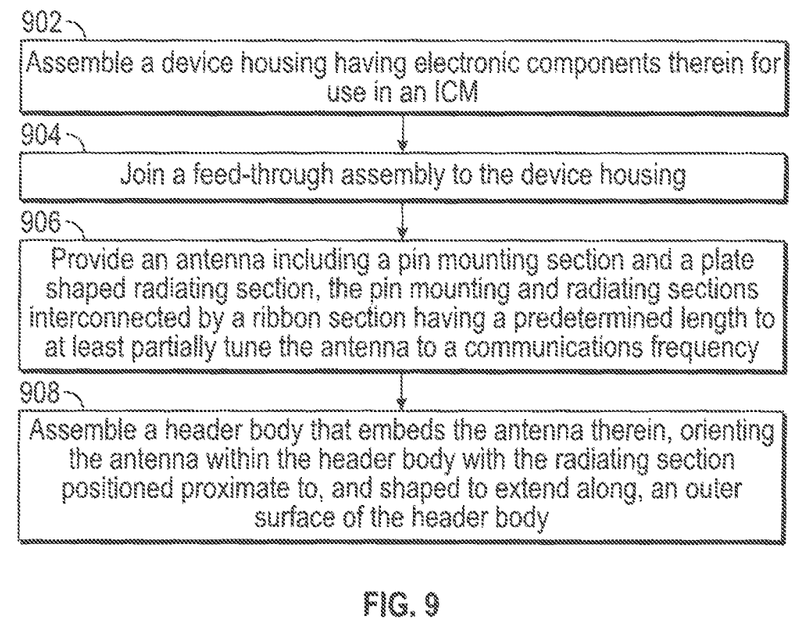
FIG. 9 illustrates a method for providing an implantable cardiac monitoring device in accordance with embodiments herein.

FIG. 9 illustrates a method for providing an implantable cardiac monitoring device in accordance with embodiments herein. At 902, the process includes assembling a device housing having electronic components therein. Examples of the various electronic components are described herein. The electronic components may include sensing circuitry to sense cardiac signals of interest, one or more processors to perform monitoring operations, transceiver circuitry to communicate with external devices and other components as described herein and/or understood by one of ordinary skill in the art. The memory, processors, and other electronic components are within a housing formed of a biocompatible material.

At 904, the process includes joining a feedthrough assembly to the device housing. The housing includes a feedthrough opening at one end and a battery attachment at the opposite end. A hermetically sealed battery is welded to the battery attachment surface, and a feedthrough is welded to the feedthrough opening, thereby hermetically sealing the interior of the housing.

At 906, an antenna is provided including a pin mounting section and a plate shaped radiating section. The pin mounting and radiating sections are interconnected by a ribbon section having a predetermined length to at least partially tune the antenna to a communications frequency. Optionally, the radiating section is sized as a rectangular plate with a width that is wider than a width of the ribbon section to provide large radiating edges long the plate and to provide a stabilizing force for anchoring and retention of the header on the device housing. Additionally, or alternatively, the providing operation includes shaping the radiating section as an elongated rectangular-shaped plate that extends along a longitudinal axis, and bending the plate along the longitudinal axis in an arc that is shaped to follow a contour of the outer surface of the header body. Additionally, or alternatively, the providing operation includes stamping the antenna with the ribbon section to have a narrower width than a width of the radiating sections. Optionally, the providing operation includes stamping the pin mounting section to have a plate shape and aligning the plate shape with a pin that projects from the feedthrough assembly. Optionally, a zig-zag pattern is formed in the ribbon section with a predetermined length to at least partially tune the antenna to a frequency of interest.

At 908, the header body is assembled by embedding the antenna within the header. Within the assembled header body, the antenna is oriented with the radiating section positioned proximate to, and shaped to extend along, an outer surface of the header body. Optionally, the antenna includes an overall length extending from a proximal end of the pin mounting section to a distal end of the radiating section, the method further comprising tuning the antenna by adjusting the overall length based on a communications frequency to carry RF signals. Optionally, the assembling operation comprises injection molding or casting a flowable material about the antenna.

The various methods as illustrated in the FIGS and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The specification and drawings are, accordingly, to be regarded in an illustrative rather than a restrictive sense. It will, however, be evident that various modifications and changes may be made thereunto without departing from the broader spirit and scope of the embodiment as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the embodiment to the specific form or forms disclosed, but on the contrary, the intention is to cover all modifications, alternative constructions and equivalents falling within the spirit and scope of the embodiment, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising." or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiment without departing from its scope. While the dimensions, types of materials and coatings described herein are intended to define the parameters of the embodiment, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. An implantable cardiac monitoring device, comprising:
a device housing having electronic components therein;
a feedthrough assembly joined to the device housing;
an antenna; and
a header body that includes a housing mounting surface mounted to the device housing proximate to the feedthrough assembly, the header body enclosing the antenna and feedthrough assembly;
the antenna including a pin mounting section and a plate shaped radiating section, the pin mounting and radiating sections interconnected by a ribbon section, the ribbon section length being configured so that an electrical length of the antenna is tuned to a communication frequency, the radiating section being elongated in a first direction along a first longitudinal axis positioned proximate to and shaped to follow a contour of a peripheral edge of the header body, the peripheral edge located remote from the housing mounting surface.

2. The device of claim 1, wherein the radiating section is arc shaped in a second direction relative to the first longitudinal axis to follow a curve in the contour of the peripheral edge of the header body.

3. The device of claim 1, wherein the ribbon section has a narrower width than a width of the radiating section.

4. The device of claim 1, wherein the pin mounting section is plate shaped and oriented to align with a pin that projects from the feedthrough assembly.

5. The device of claim 1, wherein the ribbon section includes a zig-zag pattern with a predetermined length configured so that the electrical length of the antenna is tuned to approximately equal to a quarter of a wavelength of the communication frequency.

6. The device of claim 1, wherein the antenna is curved with the pin mounting section and radiating section spaced apart to span a height of the header body from the feedthrough assembly to the curved peripheral edge of the header body.

7. The device of claim 1, wherein the header body is formed of an injection molded flowable material that embeds the antenna therein.

8. The device of claim 1, wherein the radiating section includes one or more mechanical anchoring tabs that are bent to extend inward and be securely encased within the header body.

9. The device of claim 1, wherein the electronic components include a transceiver circuit to communicate with an external device through the antenna utilizing at least one of a Bluetooth protocol or Medical Implant Communications Standard (MICS) protocol.

10. A method for providing an implantable cardiac monitoring device, comprising:
assembling a device housing having electronic components therein;
joining a feedthrough assembly to the device housing;
providing an antenna including a pin mounting section and a plate shaped radiating section, the plate shaped radiating section elongated in a first direction along a first longitudinal axis, the pin mounting and radiating sections interconnected by a ribbon section, the ribbon section length being configured so that an electrical length of the antenna is tuned to a communications frequency;
assembling a header body that embeds the antenna therein, wherein the header body includes a housing mounting surface mounted to the device housing proximate to the feedthrough assembly; and
orienting the antenna within the header body with the radiating section positioned proximate to, and following a contour of, the peripheral edge of the header body, the peripheral edge located remote from the housing mounting surface.

11. The method of claim 10, further comprising sizing the radiating section as a rectangular plate with a width that is wider than a width of the ribbon section to provide large radiating edges along the plate and to provide a stabilizing force for anchoring and retention of the header on the device housing.

12. The method of claim 10, wherein the providing operation includes bending the plate in a second direction relative to the first longitudinal axis in an arc that is shaped to follow an arc shaped contour of the peripheral edge of the header body.

13. The method of claim 10, wherein the providing operation includes stamping the antenna with the ribbon section to have a narrower width than a width of the radiating sections.

14. The method of claim 10, wherein the providing operation includes stamping the pin mounting section to have a plate shape and aligning the plate shape with a pin that projects from the feedthrough assembly.

15. The method of claim 10, further comprising forming a zig-zag pattern in the ribbon section with a predetermined length to at least partially tune the antenna to a frequency of interest.

16. The method of claim 10, wherein the antenna includes an overall length extending from a proximal end of the pin mounting section to a distal end of the radiating section, the method further comprising tuning the antenna by adjusting the overall length based on a communications frequency to carry RF signals.

17. An implantable cardiac monitoring device, comprising:
a device housing having electronic components therein;
a feedthrough assembly joined to the device housing;
an antenna; and
a header body mounted to the device housing and enclosing the antenna and feedthrough assembly, wherein the header body includes opposed sides that are generally planar and oriented to extend along a header plane;
the antenna including a pin mounting section and a plate shaped radiating section, the pin mounting and radiating sections interconnected by a ribbon section, the ribbon section length being configured so that an electrical length of the antenna is tuned to a communication frequency, the radiating section being elongated along a longitudinal axis positioned proximate to and shaped to follow a contour of a peripheral edge of the header body, the radiating section extending straight in a first direction along the header plane.

18. A method for providing an implantable cardiac monitoring device, comprising:
assembling a device housing having electronic components therein;
joining a feedthrough assembly to the device housing;
providing an antenna including a pin mounting section and a plate shaped radiating section, the pin mounting and radiating sections interconnected by a ribbon section, the ribbon section length being configured so that an electrical length of the antenna is tuned to a communications frequency;

assembling a header body that embeds the antenna therein, wherein the header body includes opposed sides that are generally planar and oriented to extend along a header plane; and orienting the antenna within the header body with the radiating section positioned proximate to, and elongated to follow a contour of, a peripheral edge of the header body, the radiating section extending straight in a first direction along the header plane.

\* \* \* \* \*